US011439756B2

(12) United States Patent
Glenting et al.

(10) Patent No.: US 11,439,756 B2
(45) Date of Patent: Sep. 13, 2022

(54) FLOW COMMUNICATION UNIT WITH PRESERVATIVE

(71) Applicant: Novo Nordisk A/S, Bagsvaerd (DK)

(72) Inventors: Vera Pinto Glenting, Copenhagen (DK); Joern Drustrup, Farum (DK); Henrik Bengtsson, Taastrup (DK); Jonas Kildegaard Pedersen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 268 days.

(21) Appl. No.: 16/641,883

(22) PCT Filed: Aug. 20, 2018

(86) PCT No.: PCT/EP2018/072400
§ 371 (c)(1),
(2) Date: Feb. 25, 2020

(87) PCT Pub. No.: WO2019/042802
PCT Pub. Date: Mar. 7, 2019

(65) Prior Publication Data
US 2020/0246547 A1 Aug. 6, 2020

(30) Foreign Application Priority Data

Aug. 30, 2017 (EP) ..................................... 17188590

(51) Int. Cl.
*A61M 5/24* (2006.01)
*A61M 5/00* (2006.01)
(Continued)

(52) U.S. Cl.
CPC .......... *A61M 5/2459* (2013.01); *A61M 5/001* (2013.01); *A61M 5/2448* (2013.01);
(Continued)

(58) Field of Classification Search
CPC .. A61M 5/345; A61M 5/2459; A61M 5/2466; A61M 5/3293; A61M 5/3295; A61M 5/3297; A61M 5/344
See application file for complete search history.

(56) References Cited

U.S. PATENT DOCUMENTS 3,354,881 A * 11/1967 Bloch ................... A61M 5/326
604/199
4,133,457 A 1/1979 Klassen
(Continued)

FOREIGN PATENT DOCUMENTS

CN 1744871 A 3/2006
CN 1764798 A 4/2006
(Continued)

*Primary Examiner* — Nilay J Shah
(74) *Attorney, Agent, or Firm* — Wesley Nicolas

(57) ABSTRACT

An assembly includes a sealed drug reservoir unit, a subcutaneous flow conducting device in the form of a needle unit or an infusion set, and a flow communication unit. The flow communication unit includes a proximal hollow needle adapted to penetrate a needle-penetrable septum of the reservoir, a first flow-way inflow communication with the proximal needle and comprising a pressure-controlled valve, a second flow-way in flow communication with the first flow-way, an amount of preservative arranged to react with a substance received by the second flow-way, and distal flow communication structure adapted to provide flow communication between the second flow-way and the needle unit. The valve is controlled to open when the reservoir is pressurized, the preservative being provided to react with substances introduced to the second flow way via the needle unit.

13 Claims, 8 Drawing Sheets

(51) Int. Cl.
*A61M 5/34* (2006.01)
*A61M 5/162* (2006.01)
*A61M 5/32* (2006.01)
*A61M 39/16* (2006.01)

(52) U.S. Cl.
CPC ............ *A61M 5/345* (2013.01); *A61M 5/162* (2013.01); *A61M 5/3297* (2013.01); *A61M 39/162* (2013.01); *A61M 2205/3337* (2013.01)

(56) References Cited

U.S. PATENT DOCUMENTS

| | | | |
|---|---|---|---|
| 4,919,658 A * | 4/1990 | Badia | A61M 5/162 604/199 |
| 5,340,359 A * | 8/1994 | Segura Badia | A61M 39/162 604/905 |
| 6,871,838 B2 | 3/2005 | Raines et al. | |
| 7,291,133 B1 | 11/2007 | Kindler et al. | |
| 7,981,081 B2 | 7/2011 | Marsh et al. | |
| 8,066,692 B2 | 11/2011 | Simpson et al. | |
| 8,863,993 B2 | 10/2014 | Donnette et al. | |
| 8,863,998 B2 | 10/2014 | Painchaud et al. | |
| 9,241,828 B2 | 1/2016 | Pardes et al. | |
| 9,408,971 B2 | 8/2016 | Carlyon | |
| 10,112,018 B2 | 10/2018 | Cowe | |
| 2004/0158204 A1 | 8/2004 | Reboul | |
| 2005/0043684 A1* | 2/2005 | Basta | A61M 25/09041 604/167.03 |
| 2005/0113750 A1 | 5/2005 | Targell | |
| 2011/0168170 A1 | 7/2011 | Patton et al. | |
| 2011/0208128 A1 | 8/2011 | Wu et al. | |
| 2013/0018323 A1* | 1/2013 | Boyd | A61M 5/2448 604/407 |
| 2016/0001014 A1 | 1/2016 | Eilertsen et al. | |
| 2020/0246547 A1 | 8/2020 | Glenting et al. | |
| 2021/0030966 A1 | 2/2021 | Bengtsson et al. | |
| 2021/0077727 A1 | 3/2021 | Bengtsson et al. | |

FOREIGN PATENT DOCUMENTS

| | | |
|---|---|---|
| CN | 2910250 Y | 6/2007 |
| CN | 104703640 A | 6/2015 |
| CN | 102844073 | 11/2015 |
| EP | 0716860 A3 | 11/1996 |
| EP | 0795342 A2 | 9/1997 |
| EP | 1948523 A1 | 7/2008 |
| EP | 2704773 A1 | 3/2014 |
| GB | 706150 A | 3/1954 |
| GB | 739753 A | 11/1955 |
| WO | 2007056233 A1 | 5/2007 |
| WO | 2012152703 A1 | 11/2012 |
| WO | 2013112486 A1 | 8/2013 |
| WO | 2014009444 A1 | 1/2014 |
| WO | 2014064100 A1 | 5/2014 |
| WO | 2014125067 A1 | 8/2014 |
| WO | 2015155229 A1 | 10/2015 |
| WO | 2015173151 A1 | 11/2015 |
| WO | 2015177082 | 11/2015 |
| WO | 2016061062 A1 | 4/2016 |
| WO | 2016131954 | 8/2016 |
| WO | 2017032599 A1 | 3/2017 |
| WO | 2017050694 | 3/2017 |
| WO | 2017129314 | 8/2017 |
| WO | 2018085952 | 5/2018 |

* cited by examiner

FLOW COMMUNICATION UNIT WITH PRESERVATIVE

CROSS-REFERENCE TO RELATED APPLICATIONS

This application is a 35 U.S.C. § 371 National Stage application of International Application PCT/EP2018/072400 (published as WO 2019/042802), filed Aug. 20, 2018, which claims priority to European Patent Application 17188590.8, filed Aug. 30, 2017, the contents of all above-named applications are incorporated herein by reference.

The present invention relates to medical delivery devices adapted for transcutaneous delivery of an amount of drug. In a specific aspect the invention relates to a preservative-containing flow communication unit to be used in combination with or forming part of a drug delivery assembly.

BACKGROUND OF THE INVENTION

In the disclosure of the present invention reference is mostly made to the treatment of diabetes by delivery of liquid insulin formulation, however, this is only an exemplary use of the present invention.

Drug delivery devices in the form of drug injection devices have greatly improved the lives of patients who must self-administer liquid drugs and biological agents. Drug injection devices may take many forms, including simple disposable devices that are little more than an ampoule with an injection means or they may be highly sophisticated electronically controlled instruments with numerous functions. Some devices are intended for single-use and may come with an integrated needle, e.g. comprising a so-called pre-filled syringe. However, in case the drug delivery device is intended to be used for multiple injections, it will typically be designed for use with a replaceable needle or cannula unit which ideally is to be replaced for each injection of a dose of drug. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. While pen-style injection devices are typically cylindrically shaped with a mounted needle protruding from the most distal portion of one end of the device, some devices have other shapes with the needle no longer protruding from the most distal part of an end of the device, e.g. Innovo® and InnoLet® from Novo Nordisk A/S, Bagsvrd, Denmark.

Typically, injection devices use a pre-filled cartridge containing the liquid medication of interest, e.g. 1.5 or 3.0 ml of insulin or growth hormone formulation. The cartridge is typically in the form of a generally cylindrical transparent glass cylinder having a distal bottle neck portion with a distal opening closed by a needle pierceable septum and an opposed proximal opening in which an elastomeric piston is received, the piston being arranged to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded.

As described above, a drug delivery device intended to be used for multiple injections is typically designed to be used in combination with a replaceable needle unit comprising a proximal needle portion adapted to be inserted into the drug-filled cartridge through a needle-penetrable septum seal and a distal needle portion adapted to be introduced subcutaneously, this allowing a given dose amount of liquid drug formulation to be injected subcutaneously through the hollow needle. Since the proximal needle portion penetrates the seal of the cannula and provides a flow path from the inside of the cannula to the outside, a risk of contamination of the cartridge contents is introduced.

The risk of contamination is primarily related to removal of the needle unit after use. As long as the cannula is penetrating the cartridge seal, it provides access from surroundings to the drug formulation and should thus be removed immediately after injection. However, after injection but prior to removal of the needle, the small volume of drug formulation inside the needle itself may be contaminated either from body fluids or from bacteria in the surroundings when the cannula is extracted from the skin of the user. When the cannula is removed from the cartridge, some of the remaining fluid in the cannula may be sucked into the cartridge, thereby contaminating the drug formulation in the cartridge.

Therefore, drug formulations for use in multi dose injection devices must contain a sufficient level of preservatives to insure biostatic conditions during the expected in-use time of the cartridge to counter such contamination. This requirement is included in chapters on injectable drug formulations in current versions of international pharmacopeia.

The use of preservatives may in some cases reduce the efficacy of the drug and in some cases be incompatible with the drug, which means that such type of drug formulations cannot be used with a multi-dose injection device. For example, the necessary preservatives would destroy the drug substance in the cartridge by precipitating the drug substance or chemically react with it.

Having regard to the above, it is an object of the present invention to provide components, devices and methods which enables the use of drug formulations with little or no preservatives in cartridges to be used in multi-dose drug delivery devices adapted to be used in combination with replaceable subcutaneous needle units. It is a specific object of the invention to provide means allowing the above to be realized in a user-friendly and cost-effective way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a general aspect of the invention an assembly is provided, comprising a reservoir with a drug-filled interior and an outlet, a flow conducting device, and a flow communication unit adapted to provide flow communication between the cartridge and the flow conducting device. The flow conducting device comprises a hollow tubular structure with a skin-piercing distal end, and a proximal flow inlet. The flow communication unit comprises a proximal inlet adapted to be arranged in flow communication with the reservoir, a first flow way in flow communication with the proximal inlet and comprising pressure-controlled valve means, a second flow way in flow communication with the first flow way, an amount of preservative arranged to react with a substance received by the second flow way, and distal flow communication means adapted to provide flow communication between the second flow way and the flow conducting device flow inlet. A combined flow way can be established between the reservoir interior and the expelling needle via the proximal inlet and the first and second flow ways when the reservoir, the flow communication unit and the flow conducting device are connected to each other. The valve means is controlled to open when the cartridge interior is pressurized. The preservative can react with a substance introduced to the second flow way via the expelling needle.

By such an arrangement the likelihood of contamination of the reservoir would be reduced, this allowing the use of drug formulations with little or no preservatives in reservoirs to be used in multi-dose drug delivery devices adapted to be used in combination with replaceable subcutaneous flow conducting devices.

In a further aspect the flow conducting device is a needle unit, wherein the hollow tubular structure is a hollow expelling needle with a skin-piercing distal end.

In a specific aspect of the invention an assembly is provided comprising a cartridge with a drug-filled interior, a needle unit, and a flow communication unit adapted to provide flow communication between the cartridge and the needle unit. The drug-filled cartridge comprises an outlet sealed by a needle-penetrable septum. The needle unit comprises a hollow expelling needle with a skin-piercing distal end, and a proximal flow inlet. The flow communication unit comprises a proximal hollow needle adapted to penetrate the needle-penetrable septum, a first flow way in flow communication with the proximal needle and comprising pressure-controlled valve means, a second flow way in flow communication with the first flow way, an amount of preservative arranged to react with a substance received by the second flow way, and distal flow communication means adapted to provide flow communication between the second flow way and the needle unit flow inlet. A combined flow way can thereby be established between the cartridge interior and the expelling needle via the proximal needle and the first and second flow ways when the cartridge, the flow communication unit and the needle unit are connected to each other. The valve means is controlled to open when the cartridge interior is pressurized, and the preservative can react with a substance introduced to the second flow way via the expelling needle. Depending on the specific design of second flow way, the preservative may react with a substance received by an inner and/or an outer surface of the second flow way.

In a first exemplary embodiment the flow communication unit comprises a tubular conduit comprising a distal portion with an open end, the tubular conduit forming the second flow way, and a preservative unit comprising an amount of preservative and having a first axial position in which the hollow conduit distal portion is embedded in preservative, and a second axial position in which the hollow conduit distal portion protrudes distally from the preservative unit. The preservative unit can be moved from the first to the second position when the needle unit is connected to the flow communication unit, the hollow conduit distal portion thereby providing the distal flow communication means.

The preservative unit may comprise a reservoir with an amount of fluid preservative. The reservoir may be provided with a needle-penetrable septum portion adapted to be penetrated by the hollow conduit distal portion when the preservative unit is moved from the first to the second position. The preservative unit may be provided with biasing means returning the preservative unit from the second to the first position when the needle unit is disconnected from the flow communication unit.

In a second exemplary embodiment the needle unit comprises a tubular conduit comprising a proximal portion with an open end forming the proximal flow inlet, and the second flow way of the flow communication unit is adapted to receive the tubular conduit proximal portion when the needle unit is connected to the flow communication unit. The second flow way may be in the form of a conduit comprising an amount of fluid preservative, the conduit being closed by a septum adapted to be penetrated by the tubular conduit proximal portion when the needle unit is connected to the flow communication unit.

The flow communication unit may comprise a reservoir with an amount of fluid preservative, a preservative flow communication being provided between the conduit and the reservoir, wherein the preservative flow communication is operated between an initial open state and an operational closed state when the needle unit is connected to the flow communication unit. The flow communication unit septum may be flexible allowing it to be moved axially from an initial distal position to a proximal operational position to thereby close the preservative flow communication when the needle unit is connected to the flow communication unit.

In a further aspect the flow conducting device is an infusion set, wherein the hollow tubular structure is a catheter with a hollow expelling needle with a skin-piercing distal end. In this way the flow communication unit can be used in connection with a pump system infusing a medicament through an infusion set.

In the above an assembly has been described, however, the described flow communication unit may also be provided as a separate unit per se. Correspondingly, in a further aspect of the invention a flow communication unit is provided, comprising a proximal hollow needle adapted to penetrate a needle-penetrable septum, a first flow way in flow communication with the proximal needle and comprising pressure-controlled valve means, a second flow way in flow communication with the first flow way, an amount of preservative arranged to react with a substance received by the second flow way, and distal flow communication means adapted to provide flow communication between the second flow way and a flow conducting device flow inlet, wherein the valve means is controlled to open when the proximal hollow needle is pressurized.

In an exemplary embodiment the flow conducting device flow inlet may be the inlet of a needle unit or an infusion set.

In an exemplary embodiment the flow communication unit further comprises a tubular conduit comprising a distal portion with an open end, the tubular conduit forming the second flow way, and a preservative unit comprising an amount of preservative and having a first axial position in which the hollow conduit distal portion is embedded in preservative, and a second axial position in which the hollow conduit distal portion protrudes distally from the preservative unit. The preservative unit may be provided with a reservoir with an amount of fluid preservative, the reservoir comprising a needle-penetrable septum portion adapted to be penetrated by the hollow conduit distal portion when the preservative unit is moved from the first to the second position.

In a further exemplary embodiment the second flow way of the flow communication unit is in the form of a conduit comprising an amount of fluid preservative, the conduit being closed by a needle-penetrable septum, either permanently or when the flow communication unit is operated between an initial and an operational state.

The flow communication unit may further comprise a reservoir with an amount of fluid preservative, wherein a preservative flow communication is provided between the conduit and the reservoir. This allows the preservative flow communication to be operated between an initial open state and an operational closed state. The septum may be flexible and can be moved axially from an initial distal position to a proximal operational position to thereby close the preservative flow communication.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

Figure 1A:
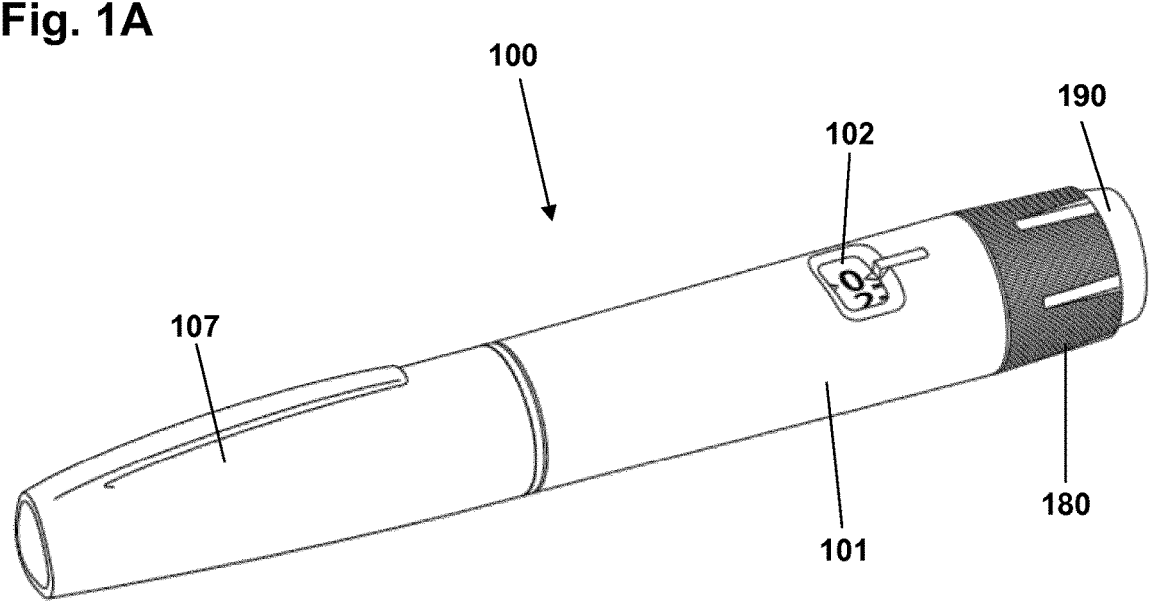
FIGS. 1A and 1B show an embodiment of a drug delivery device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a "generic" prior art resettable dial-up/dial down automatic drug delivery device will be described, such a device providing the basis for the exemplary embodiment of the present invention.

The pen device 100 comprises a cap part 107 and a main part having a proximal body or drive assembly portion with a housing 101 in which a drug expelling mechanism is arranged or integrated, and a distal cartridge holder portion 110 in which a drug-filled transparent cartridge 120 with a distal needle-penetrable septum is arranged and retained in place by a cartridge holder attached to the proximal portion, the cartridge holder having a pair of opposed openings 111 allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the shown embodiment is in the form of a ratchet mechanism. When the user desires to expel the set dose the button is actuated whereby the drive member is brought into engagement with the piston rod drive mechanism and the holding mechanism subsequently released.

Figure 1B:
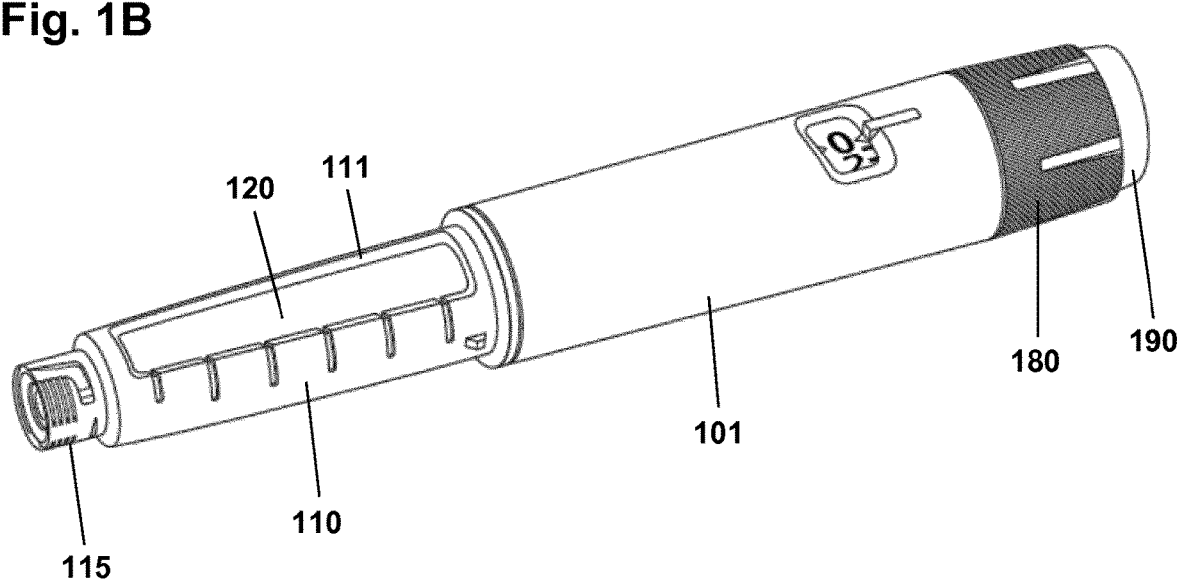

Although FIGS. 1A and 1B show a drug delivery device of the pre-filled type, i.e. it is supplied with a pre-mounted cartridge and is to be discarded when the cartridge has been emptied, in alternative embodiments the drug delivery device may be a durable device designed to allow a cartridge assembly to be replaced, e.g. in the form of a cartridge assembly comprising a cartridge mounted in a cartridge holder. Such an assembly may further be provided with a pre-mounted piston rod.

Preservatives are normally needed to ensure static microbial conditions. In products from Novo Nordisk A/S, one or both of the preservatives phenol and m-cresol are used to ensure that minor microbial contaminations will not grow during the expected lifetime of a multi dosed injectable. However, phenol and m-cresol are toxic (which is required for them to work as intended) and may therefore as a side effect cause injection site reactions, or in some cases allergic reactions. This also means that additional restrictions applies to the selection of new protein/peptide drugs, since they are required to be preservative stabile, especially when the drug product is intended for daily or weekly use. Thus, it would in some cases be preferable to be able to reduce or omit the adding of preservatives to a given drug. It should be noted that substances that are regarded as preservatives may be added in lower amounts with the purpose of acting as stabilizer of the drug substance, e.g. insulin substances.

To ensure antimicrobial requirements can be met without adding preservatives to the drug itself, two major issues must be addressed. Firstly, it must be ensured that a contaminated needle or cannula cannot be inserted in the cartridge and introduce microbial contamination of the cartridge. Secondly, it must be ensured that backflow through the cannula is not possible which would introduce a risk of microbial contamination through backflow of body fluids from the user. This concept should not be confused with known arrangements in which preservative-filled reservoirs are provided to allow a subcutaneous needle to safely be used more than once, e.g. as disclosed in U.S. Pat. No. 3,354,881 and WO 2014/064100.

In a first exemplary embodiment of the invention, a drug delivery assembly is modified by adding a valve/preservative flow communication unit between the needle unit and the device. This enables production of the same device for use both with and without preservatives in the drug. In products where preservatives can be added without drawbacks, the valve/preservative unit can simply be omitted.

Thus, with reference to FIGS. 2A to 2E a first exemplary embodiment of the invention in the form of an assembly will be described. The assembly 200 comprises a cartridge unit 210, a needle unit 220, and a flow communication unit 230 adapted to provide flow communication between the cartridge unit and the needle unit.

Figure 2A:
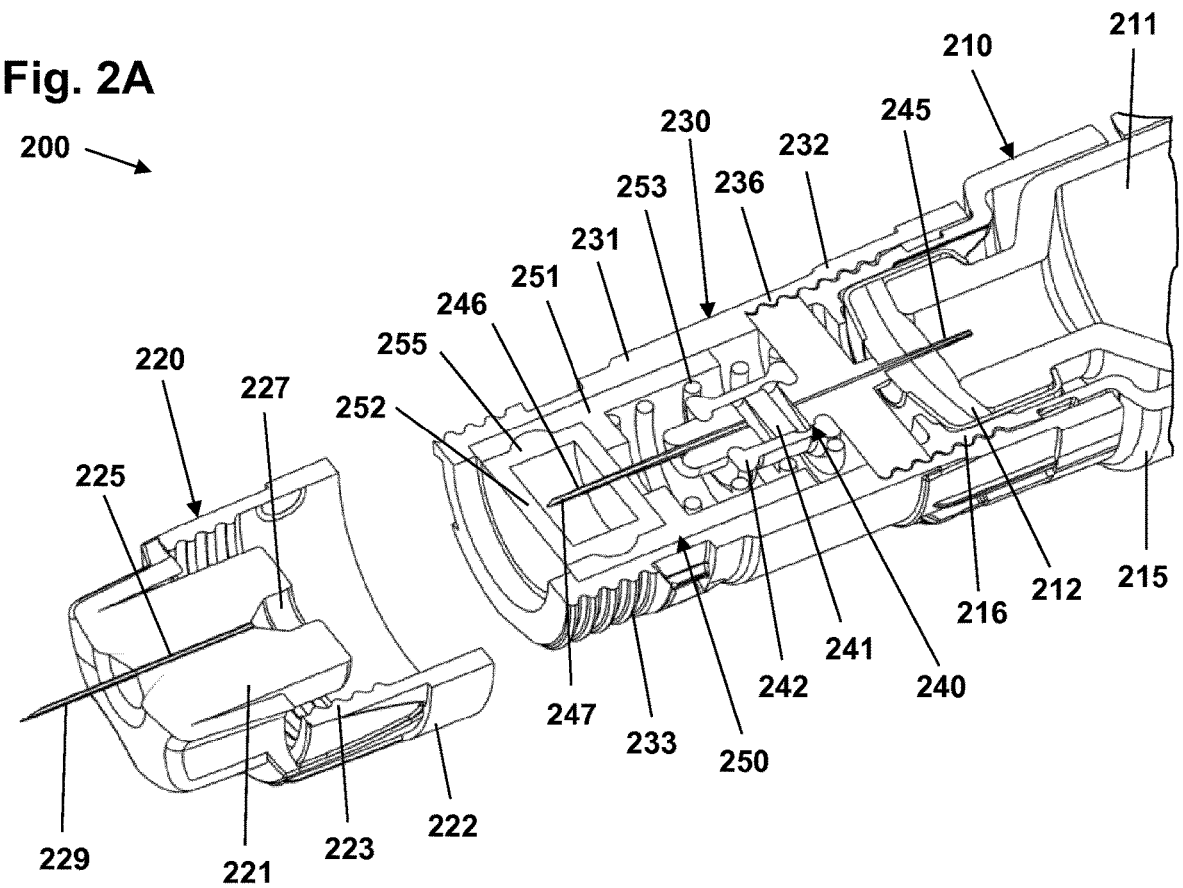
FIGS. 2A-2E show in cross-sections a first embodiment of a drug delivery assembly in different states of use.

In the shown embodiment the cartridge unit 210 is in the form of a drug delivery device of the general type described with reference to FIGS. 1A and 1B. The drug delivery device which may be of the durable or prefilled type comprises a drug-filled cartridge 211 arranged in a cartridge holder 215 provided with coupling means in the form of an outer distal thread 216, the cartridge comprising an outlet sealed by a needle-penetrable septum 212 accessible through a distal opening in the cartridge holder. The septum comprises two layers, the outer layer being optimized for sealing properties, the inner layer being optimized for being inert to the liquid drug formulation contained in the reservoir. In FIG. 2A only the distal-most portions of the cartridge and the cartridge holder are shown.

The needle unit 220 comprises a distal hub portion 221 in which a hollow subcutaneous needle 225 (or expelling needle) with a skin-piercing distal end 229 and a proximal flow inlet is mounted, as well as a proximally extending skirt portion 222 with an inner thread 223 which in the shown embodiment would allow the needle unit to be mounted directly on the cartridge unit, this corresponding to the traditional use of the two units. However, as appears, the needle unit does not comprise a traditional proximal needle portion adapted to penetrate a cartridge septum. Instead the hub portion comprises a small inlet cavity 227 in flow communication with the needle flow inlet, the cavity being adapted to receive the distal needle of the flow communication unit as will be described in greater detail below.

The flow communication unit 230 comprises a cylindrical outer housing 231 in which a proximal valve assembly 240 and a distal preservative assembly 250 are arranged. The housing comprises a distal outer thread 233 adapted to engage the inner thread 223 of the needle unit as well as a proximal skirt portion 232 with an inner thread 236 adapted to engage the cartridge holder outer thread 216. Alternatively one or both of the threaded connections may be replaced with a bayonet coupling, e.g. as shown in FIG. 1B.

The valve assembly 240 comprises a valve body 241 with a pressure controlled check valve having a proximal inlet in flow communication with a proximally extending hollow inlet needle 245 adapted to penetrate the cartridge septum 212, as well as a distal outlet in flow communication with a distally extending hollow outlet needle 246 adapted to be received in the needle unit inlet cavity 227. In the shown embodiment the check valve comprises an elastic outer rubber sleeve 242 allowing a flow of fluid through the valve channels when a given pressure difference (the cracking or opening pressure) is established across the valve. As the opening pressure is below the pressure generated in the cartridge during dose expelling but well above the pressure that would be applied to the inlet needle during normal use of the assembly, the valve arrangement essentially functions as a one-way check valve for all practical purposes. In the shown embodiment the valve assembly is a separate unit, however, in alternative embodiments it may be formed fully or partly integrally with the housing.

In the shown embodiment the flow communication unit comprises a proximal inlet adapted to be arranged in flow communication with the reservoir in the form of a hollow inlet needle 245 adapted to penetrate a cartridge septum, however, in alternative embodiments the flow communication may be in the form of a valve arrangement comprised in the flow communication unit and/or cartridge unit.

The preservative assembly 250 comprises an inner housing 251 in which a preservative-containing member is mounted. In the shown embodiment the preservative-containing member is in the form of a reservoir 255 formed from a self-sealing needle-penetrable elastomeric material and contains a liquid preservative formulation. The inner housing and thus the reservoir is arranged axially moveable in the outer housing between an initial distal position and a proximal actuated position, the inner housing being biased towards the distal position by a spring 253. When the reservoir is in the initial distal position the distal end of the hollow outlet needle 246 is positioned inside the reservoir. When the reservoir is moved proximally against the force of the biasing spring the distal end of the hollow needle will sealingly penetrate the reservoir distal portion 252 from the interior thereof and protrude distally.

In FIG. 2A the first exemplary assembly is shown in an initial state in which the flow communication unit 230 has been mounted on the cartridge holder 215 with the inlet needle 245 in flow communication with the cartridge interior. As the pressure in the cartridge is below the valve opening pressure the valve is closed. The preservative assembly 250 is biased to its distal position with the distal end of the outlet needle 246 arranged in the liquid preservative formulation. The needle unit 220 has not yet been mounted on the flow communication unit.

Figure 2B:
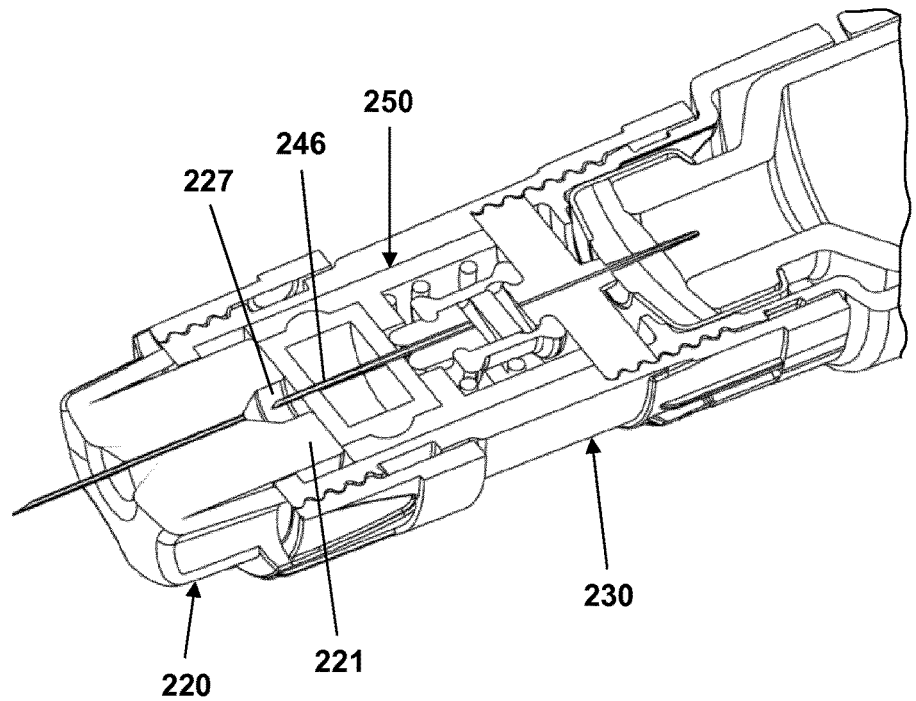

In FIG. 2B the needle unit 220 has been mounted on the flow communication unit 230 via the threaded coupling means 223, 233. During mounting the proximal portion of the needle hub portion 221 has engaged the preservative assembly 250 and moved it proximally against the force of the biasing spring, this resulting in the distal pointed end 247 of the non-moved outlet needle 246 penetrating the reservoir from the inside. When the needle unit is fully mounted the outlet needle distal end will be positioned in the hub inlet cavity 227 as shown, the cavity serving as a buffer chamber.

Figure 2C:
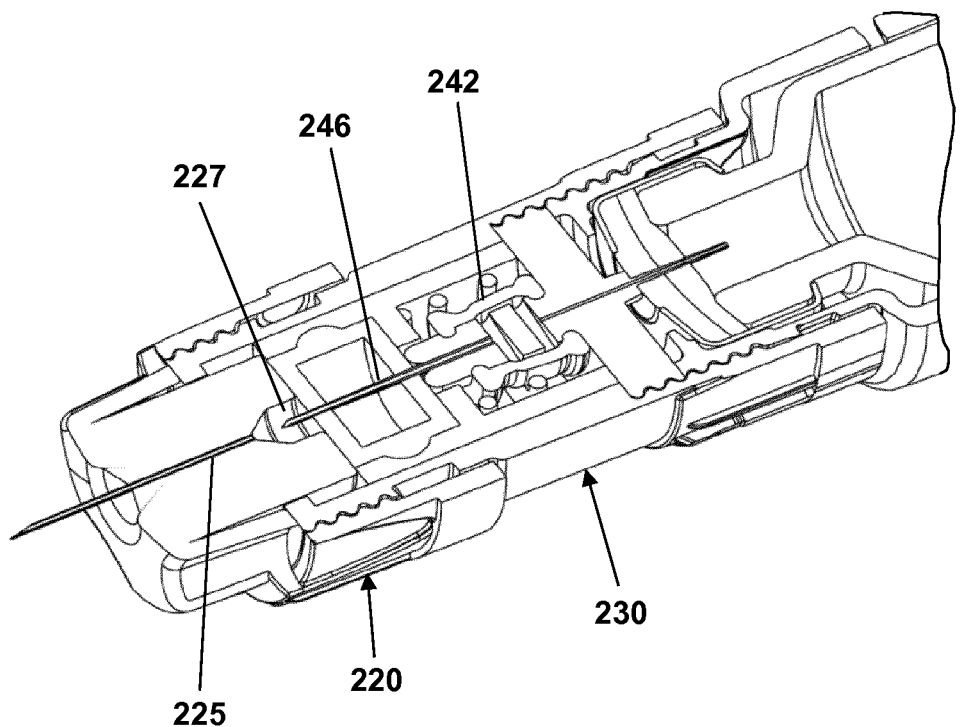

During drug expelling the increased pressure in the cartridge will be transmitted to the valve where the rubber sleeve 242 will expand thereby enabling drug to flow through the valve and into the outlet needle 246, further into the buffer chamber 227 and subsequently through the skin-piercing distal end of the subcutaneous needle 225, this as shown in FIG. 2C. The buffer chamber as well as the subcutaneous needle makes out a "dead volume" that is expelled from the cartridge but not injected. The volume should therefore be reduced to a minimum to reduce the consequences of a user neglecting to perform an air-shot prior to injection of a set dose amount of drug.

Figure 2D:
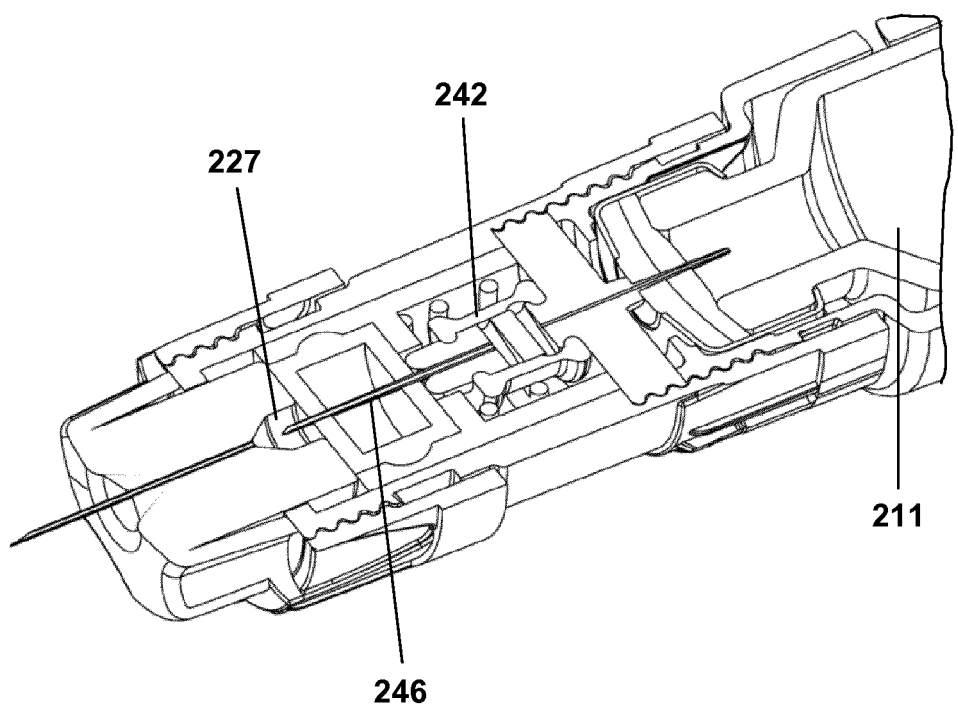

When drug expelling has ended, the pressure in the valve decreases and when the pressure drops below the elastic force of the valve rubber 242, the check valve closes, this as shown in FIG. 2D. Should any backflow of body fluids or other possibly contaminated fluids occur when pressure drops in the valve assembly channels, the contaminated fluid will enter the buffer chamber 227 and thus contaminate only the buffer chamber and the distal end of the outlet needle 246. Further, the closed check valve prevents possible backflow of preservatives and/or body fluids into the drug cartridge 211.

Figure 2E:
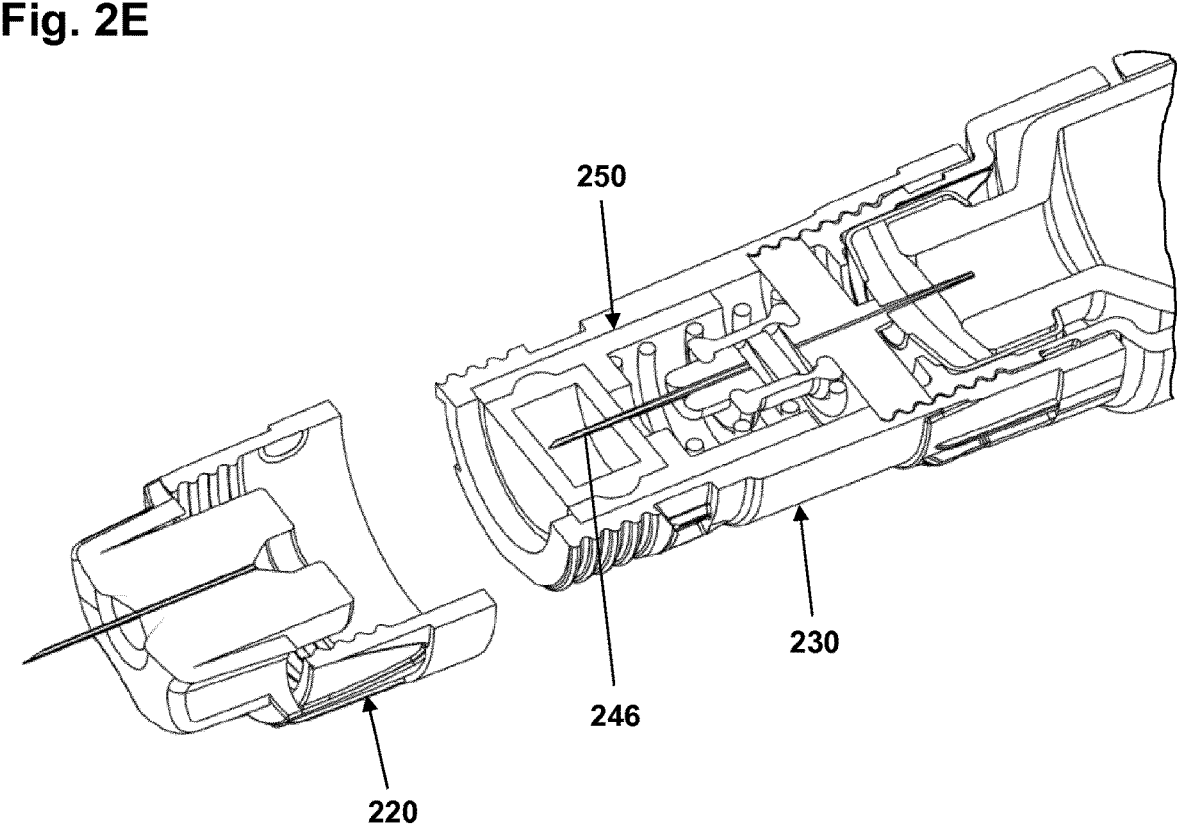

In FIG. 2E the needle unit 220 is removed from the flow communication unit 230, this allowing the spring-biased preservative assembly 250 to move distally whereby the distal end of the outlet needle 246 again will be positioned inside the preservative reservoir 255. The elastic and self-sealing properties of the material forming the preservative reservoir will ensure that any fluid and thus most of any contamination on the outer surface of the outlet needle distal end is cleaned off when the needle is retracted (relatively) into the preservative reservoir. Any remaining contamination will be countered by the preservative in which the outlet needle distal end is submerged.

Next, with reference to FIGS. 3A to 3E a second exemplary embodiment of the invention in the form of an assembly will be described. The assembly 300 comprises a cartridge unit 310, a needle unit 320, and a flow communication unit 330 adapted to provide flow communication between the cartridge unit and the needle unit.

Figure 3A:
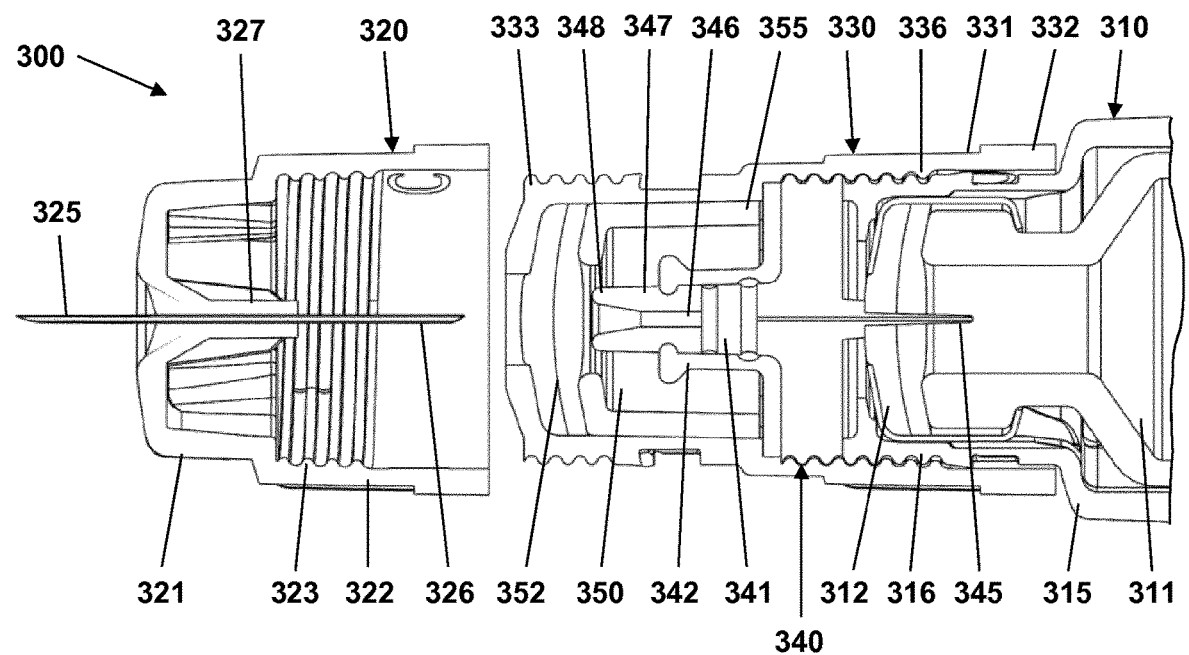
FIGS. 3A-3E show in cross-sections a second embodiment of a drug delivery assembly in different states of use.

In the shown embodiment the cartridge unit 310 is in the form of a drug delivery device of the general type described with reference to FIGS. 1A and 1B. The drug delivery device which may be of the durable or prefilled type comprises a drug-filled cartridge 311 arranged in a cartridge holder 315 provided with coupling means in the form of an outer distal thread 316, the cartridge comprising an outlet sealed by a needle-penetrable septum 312 accessible through a distal opening in the cartridge holder. In FIG. 3A only the distal-most portion of the cartridge and cartridge holder is shown.

The needle unit 320 comprises a distal hub portion 321 with a central needle mount portion 327 in which a hollow subcutaneous needle is mounted, the needle comprising a skin-piercing distal end 325 and a proximally extending pointed flow inlet portion 326, as well as a proximally extending skirt portion 322 with an inner thread 323 which in the shown embodiment would allow the needle unit to be threadedly mounted directly on the cartridge unit 310 with the proximal needle portion 326 in flow communication with the cartridge interior, this corresponding to the traditional use of the two units.

The flow communication unit 330 comprises a cylindrical outer housing 331, a proximal valve assembly 340 and a distal preservative reservoir 350. The housing comprises a distal outer thread 333 adapted to engage the thread 323 of the needle unit as well as a proximal skirt portion 332 with an inner thread 336 adapted to engage the cartridge holder thread 316. Alternatively one or both of the threaded connections may be replaced with a bayonet coupling, e.g. as shown in FIG. 1B.

The valve assembly 340 comprises a combined valve body 341 with a pressure controlled check valve having a proximal inlet in flow communication with a proximally extending hollow inlet needle 345 adapted to penetrate the cartridge septum 312, as well as a distal central tubular portion 347 forming an outlet channel 346 adapted to receive the needle unit proximal needle portion 326. As will be described below, the outlet channel 346 also serves as a preservative chamber, hence the term "combined valve body". In the shown embodiment the check valve essentially corresponds to the check valve of the first exemplary embodiment and thus comprises an elastic outer rubber sleeve 342 allowing a flow of fluid through the valve channels when a given pressure difference is established across the valve. As the opening pressure is below the pressure generated in the cartridge during dose expelling but well above the pressure that would be applied to the inlet needle during normal use of the assembly, the valve arrangement essentially functions as a one-way check valve for all practical purposes. In the shown embodiment the valve assembly is a separate unit, however, in alternative embodiments it may be formed fully or partly integrally with the housing.

The preservative reservoir comprises a distally-facing flexible needle-penetrable septum 352 having a central portion with an initial axial position. The central tubular portion 347 extends into the preservative reservoir and comprises a distal end with a circumferential sealing edge 348 adapted to engage the proximal surface of the septum central portion, however, with the septum in the initial axial position a gap is provided between the septum and the central portion and thereby a flow communication between the preservative reservoir 350 and the outlet channel/preservative chamber 346. In the shown embodiment a cylindrical support member 355 is arranged between the septum 352 and the valve assembly 340 to peripherally support the septum.

In an alternative embodiment (not shown) the flow communication unit may be formed integrally with the cartridge unit, the outer seal for the cartridge interior thus being provided by the preservative reservoir septum.

In FIG. 3A the second exemplary assembly 300 is shown in an initial state in which the flow communication unit 330 has been mounted on the cartridge holder 311 with the inlet needle 345 in flow communication with the cartridge interior. As the pressure in the cartridge is below the valve opening pressure the valve is closed. The preservative reservoir septum 352 is in the initial state with a gap formed between septum and the central portion sealing edge 348. The needle unit 320 has not yet been mounted on the flow communication unit.

Figure 3B:
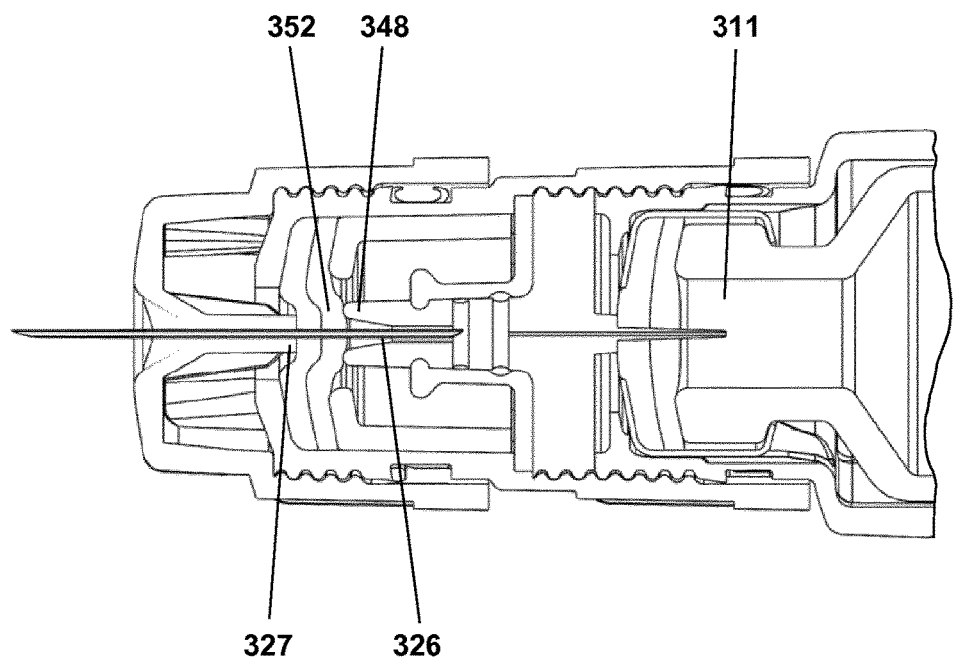

In FIG. 3B the needle unit 320 has been mounted on the flow communication unit 330 via the threaded coupling means 323, 333. During mounting the proximal needle flow inlet portion 326 penetrates the preservative reservoir septum 352 and is inserted into the outlet channel 346. Subsequently the proximal portion of the needle hub mount portion 327 engages the preservative reservoir septum 352 central portion to move it proximally into sealing engagement with the central portion sealing edge 348.

Figure 3C:
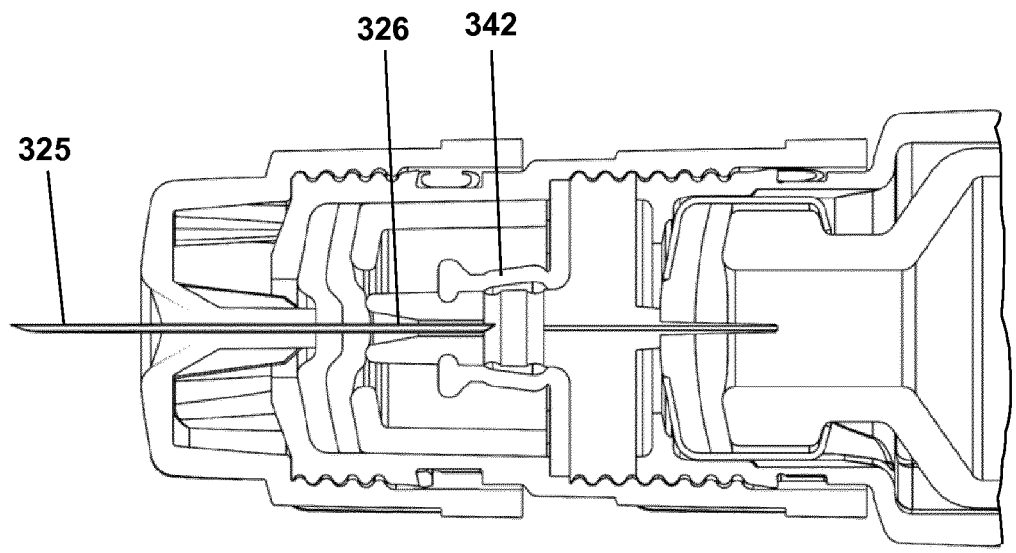

During drug expelling the increased pressure in the cartridge 311 will be transmitted to the valve where the rubber sleeve 342 will expand as shown in FIG. 3C, thereby enabling drug to flow through the valve and into the sealed outlet channel/preservative chamber 346. Since the latter is already filled with fluid, the drug has to flow into the needle flow inlet portion 326 to be expelled from the skin-piercing distal end 325. As appears, the created seal between the central portion 347 and the septum 352 prevents drug from entering the preservative reservoir 350 during drug expelling.

Figure 3D:
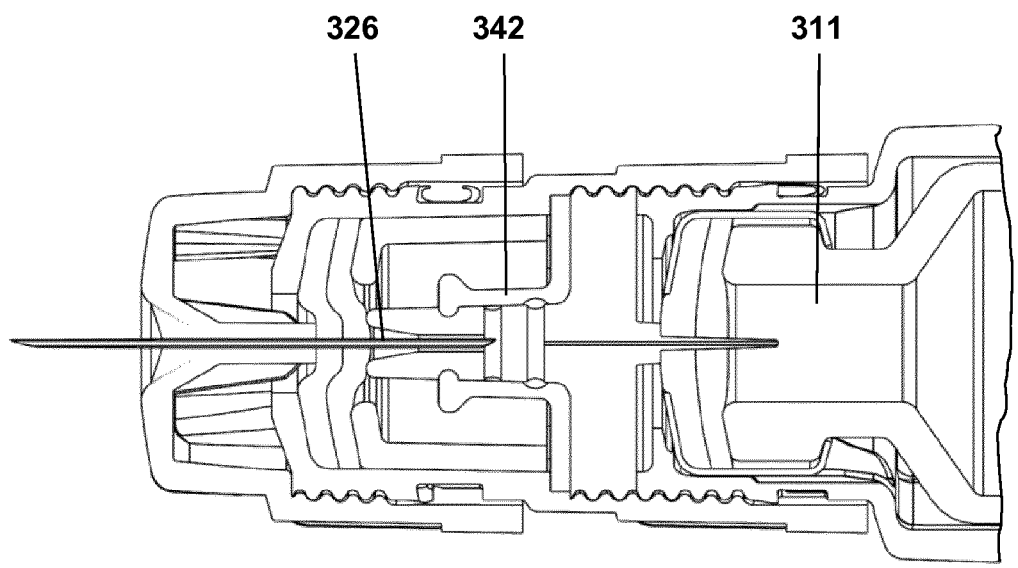

When drug expelling has ended, the pressure in the valve decreases and when the pressure drops below the elastic force of the valve rubber 342, the check valve closes, this as shown in FIG. 3D. Should any backflow of body fluids or other possibly contaminated fluids occur when pressure drops in the valve assembly channels, the contaminated fluid will enter the preservative chamber 346. Further, the closed check valve prevents possible backflow of preservatives and/or body fluids into the drug cartridge.

Figure 3E:
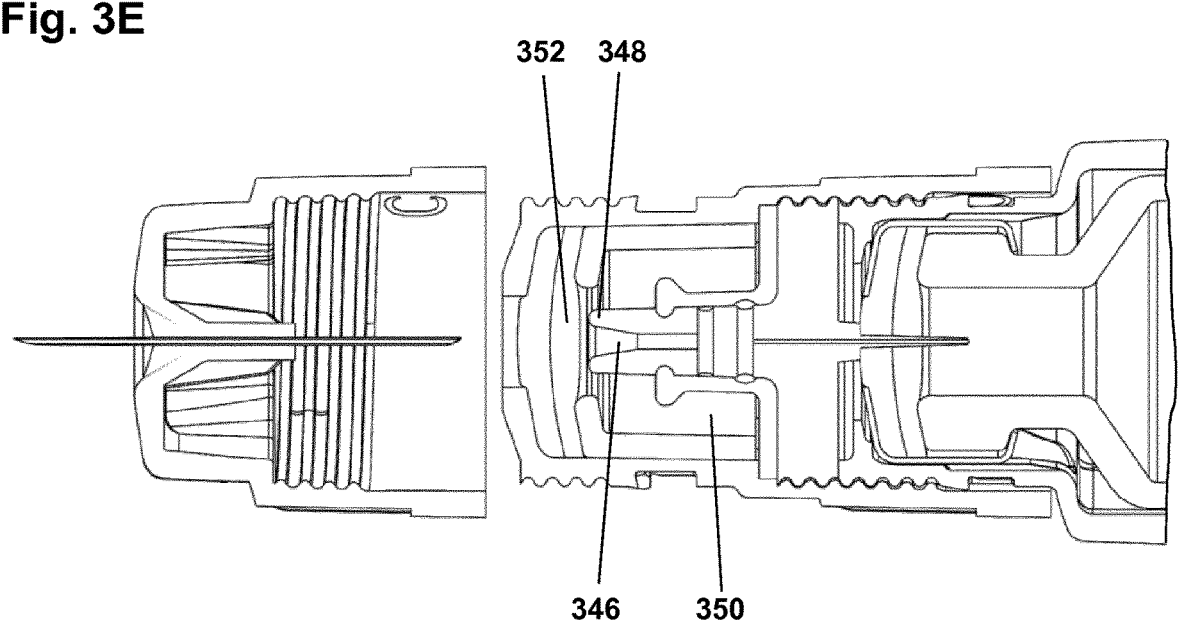

In FIG. 3E the needle unit 320 is removed from the flow communication unit 330, this allowing the preservative reservoir septum 352 central portion to return to its initial axial position and to thereby disengage the central portion sealing edge 348, thereby re-creating the initial flow communication between the preservative chamber 346 and the preservative reservoir 350, this allowing "worn" preservative fluid in the preservative chamber 346 to be exchanged/diluted with fresh preservative fluid from the much larger preservative reservoir 350, thereby restoring/maintaining the efficacy of the preservatives in the chamber.

Figure 4:
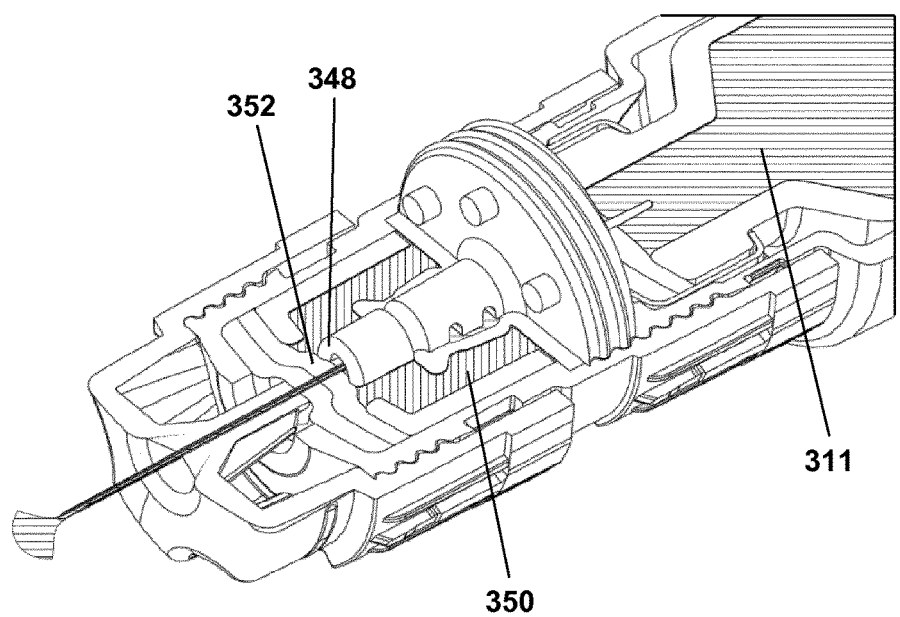
FIG. 4 shows the components of the second embodiment in an assembled state during a situation of use.

FIG. 4 shows in a cross-sectional perspective view how the cartridge drug and the fluid in the preservative reservoir are sealed from each other during drug expelling.

Turning to FIG. 5 a further exemplary embodiment will be described in which most of the functionality of the flow communication unit is provided by a single foam component.

Figure 5A:
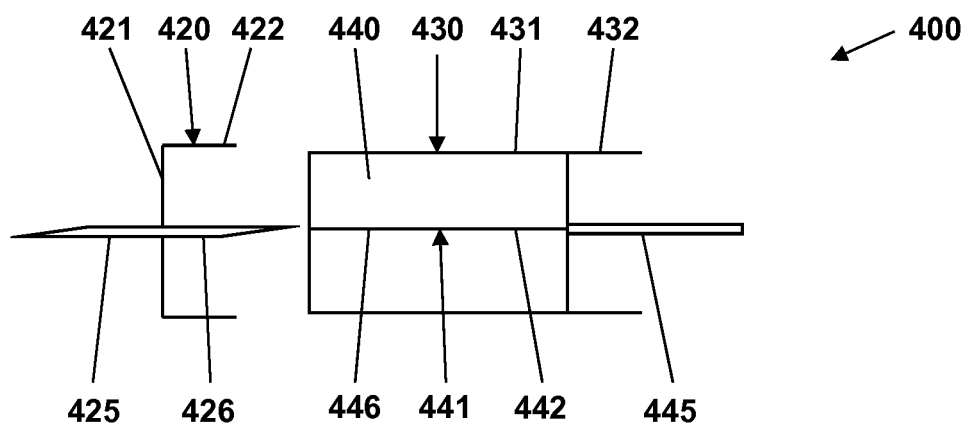
FIGS. 5A and 5B show in cross-sections a further embodiment of a drug delivery assembly in different states of use.

More specifically, FIG. 5A shows an assembly 400 comprising needle unit 420 and a flow communication unit 430 adapted to provide flow communication between a cartridge unit (not shown) and the needle unit.

The needle unit 420 comprises a hub portion 421 in which a hollow subcutaneous needle is mounted, the needle comprising a skin-piercing distal end 425 and a proximally extending flow inlet portion 426, as well as a proximally extending skirt portion 422 with an inner thread, this essentially corresponding to the needle unit of the second exemplary embodiment.

The flow communication unit 430 comprises an outer housing 431 with a distal outer thread adapted to engage the inner thread of the needle unit as well as a proximal skirt portion 432 with an inner thread adapted to engage a cartridge holder thread. In the housing a foam member 440 with a longitudinal central passageway 441 is arranged, the passageway having a distal opening and a proximal opening. In an initial state the passageway is collapsed thus providing a "virtual" channel axially through the foam member. The passageway comprises a distal portion 446 adapted to receive the needle flow inlet portion 426 of the needle unit, as well as a proximal portion 442 in flow communication with a proximally extending hollow inlet needle 445 adapted to penetrate a cartridge septum, e.g. corresponding to the above-described second exemplary embodiment.

The foam is elastically deformable allowing the passageway to expand, e.g. when a component is inserted or when subjected to an elevated pressure. The foam is impregnated with a liquid preservative formulation.

Figure 5B:
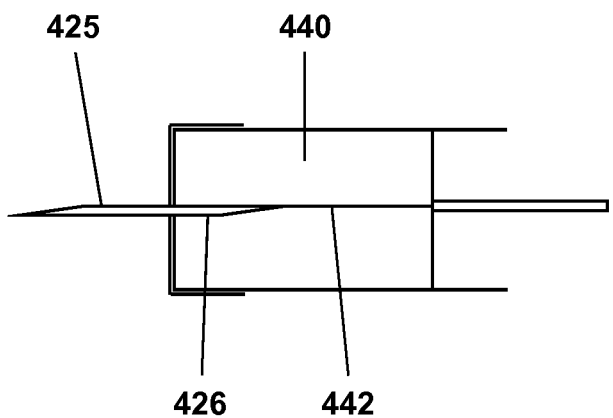

In FIG. 5B the needle unit 420 has been mounted on the flow communication unit 430 via the threaded coupling means. During mounting the proximal needle flow inlet portion 426 is inserted into the distal portion 446 of the flow member passageway 441.

During drug expelling the increased pressure in the cartridge (not shown) will be transmitted to the proximal portion 442 of the passageway where the surrounding foam will becom-pressed due to the increased pressure in the passageway and the collapsed passageway will expand, thereby enabling drug to flow through the passageway and into the inserted needle flow inlet portion 426. As the foam member has been impregnated (soaked) with liquid preservative formulation, the drug has to flow into the needle flow inlet portion to be expelled from the skin-piercing distal end 425.

When drug expelling has ended, the pressure in the proximal portion of the passageway decreases and when the pressure drops below the elastic force of the surrounding foam material and as a result the passageway will collapse. As appears, in this way the proximal portion of the passageway functions as a check valve which during use prevents possible backflow of preservatives and/or body fluids into the drug cartridge.

When the needle unit 420 is removed from the flow communication unit 430, the proximal needle flow inlet portion 426 is retracted from the distal portion of the foam member passageway allowing the expanded passageway to collapse. Any contamination that may have been introduced by the needle flow inlet portion during insertion or removal of the needle will subsequently be exposed to the preservatives contained in the foam member. The foam material used for the foam member should allow "worn" preservative fluid in the preservative passageway to be exchanged/diluted with fresh preservative fluid from the amount of preservative contained in the foam member, thereby restoring/maintaining the efficacy of the preservatives in the chamber.

In the above-described embodiment of FIG. 5A a single foam member is used which requires the foam material to be optimized for both the check valve functionality of the proximal portion of the passageway, and the preservative functionality of the distal portion of the passageway. Thus, in an alternative embodiment (not shown) a first type of foam material is used to form the proximal portion of the passageway and a second type of foam material is used to form the distal portion of the passageway, the first type of foam material being selected to optimize the valve properties of the passageway, and the second type of foam material being selected to optimize the exchange of preservative between the passageway and the surrounding body of the foam member.

LIST OF EMBODIMENTS

1. An assembly (200, 300, 400) comprising (a) a cartridge with a drug-filled interior, (b) a flow conducting device, and (c) a flow communication unit adapted to provide flow communication between the cartridge and the flow conducting device,
   (a) the drug-filled cartridge (211, 311) comprising:
   an outlet sealed by a needle-penetrable septum (212, 312),
   (b) the flow conducting device (220, 320, 420) comprising:
      a a hollow tubular structure (225, 325, 425) with a skin-piercing distal end, and
      a proximal flow inlet (227, 326, 426),
   (c) the flow communication unit (230, 330, 430) comprising:
      a proximal hollow needle (245, 345, 445) adapted to penetrate the needle-penetrable septum,
      a first flow way in flow communication with the proximal needle and comprising pressure-controlled valve means (241, 242, 341, 342, 442),
      a second flow way (246, 346, 446) in flow communication with the first flow way,
      an amount of preservative arranged to react with a substance received by the second flow way, and
      distal flow communication means (246, 352, 446) adapted to provide flow communication between the second flow way and the flow conducting device flow inlet, whereby:
a combined flow way can be established between the cartridge interior and the expelling needle via the proximal needle and the first and second flow ways when the cartridge, the flow communication unit and the flow conducting device are connected to each other,
the valve means is controlled to open when the cartridge interior is pressurized, and
the preservative can react with a substance introduced to the second flow way via the expelling needle.

2. An assembly (200, 300) as in embodiment 1, wherein the flow conducting device (220, 320, 420) is a needle unit (220, 320, 420), wherein the hollow tubular structure is a hollow expelling needle (225, 325, 425) with a skin-piercing distal end.

3. An assembly (200) as in embodiment 2, wherein the flow communication unit (230) comprises:
a tubular conduit (246) comprising a distal portion (247) with an open end, the tubular conduit forming the second flow way, and
a preservative unit (250) comprising an amount of preservative and having a first axial position in which the hollow conduit distal portion (247) is embedded in preservative, and a second axial position in which the hollow conduit distal portion (247) protrudes distally from the preservative unit,
wherein the preservative unit (250) is moved from the first to the second position when the needle unit (220) is connected to the flow communication unit (230), the hollow conduit distal portion (247) thereby providing the distal flow communication means.

4. An assembly as in embodiment 3, wherein the preservative unit comprises a reservoir (255) with an amount of fluid preservative.

5. An assembly as in embodiment 4, wherein the reservoir (255) comprises a needle-penetrable septum portion (252) adapted to be penetrated by the hollow conduit distal portion (247) when the preservative unit (250) is moved from the first to the second position.

6. An assembly as in any of embodiments 2-5, wherein the preservative unit (250) comprises biasing means (253) moving the preservative unit (250) from the second to the first position when the needle unit (220) is disconnected from the flow communication unit (230).

7. An assembly (300) as in embodiment 2, wherein:
the needle unit (320) comprises a tubular conduit (325) comprising a proximal portion (326) with an open end forming the proximal flow inlet, and
the second flow way (346) is adapted to receive the tubular conduit proximal portion when the needle unit (320) is connected to the flow communication unit (330).

8. An assembly as in embodiment 7, wherein:
the second flow way is in the form of a conduit (346) comprising an amount of fluid preservative, the conduit being closed by a septum (352) adapted to be penetrated by the tubular conduit proximal portion (325) when the needle unit is connected to the flow communication unit.

9. An assembly as in embodiment 8, wherein the flow communication unit (330) comprises:
a reservoir (350) with an amount of fluid preservative,
a preservative flow communication between the conduit (346) and the reservoir,
wherein the preservative flow communication is operated between an initial open state and an operational closed state when the needle unit (320) is connected to the flow communication unit (330).

10. An assembly as in embodiment 9, wherein:
the flow communication unit septum (352) is flexible and can be moved axially from an initial distal position to a proximal operational position to thereby close the preservative flow communication when the needle unit (320) is connected to the flow communication unit (330).

11. An assembly as in embodiment 1, wherein the flow conducting device is an infusion set, wherein the hollow tubular structure is a catheter with a hollow expelling needle with a skin-piercing distal end.

12. A flow communication unit (230, 330, 430) comprising:
a proximal hollow needle (245, 345, 445) adapted to penetrate a needle-penetrable septum,
a first flow way in flow communication with the proximal needle and comprising pressure-controlled valve means (241, 242, 341, 342, 442),
a second flow way (246, 346, 446) in flow communication with the first flow way,
an amount of preservative arranged to react with a substance received by the second flow way, and
distal flow communication means (246, 352, 446) adapted to provide flow communication between the second flow way and a flow conducting device flow inlet (227, 326, 426),
wherein the valve means is controlled to open when the proximal hollow needle is pressurized.

13. A flow communication unit (230, 330, 430) as in embodiment 12, wherein the flow conducting device flow inlet (227, 326, 426) is a needle unit flow inlet (227, 326, 426).

14. A flow communication unit as in embodiment 13, further comprising:
a tubular conduit (246) comprising a distal portion (247) with an open end, the tubular conduit forming the second flow way, and
a preservative unit (250) comprising an amount of preservative and having a first axial position in which the hollow conduit distal portion (247) is embedded in preservative, and a second axial position in which the hollow conduit distal portion (247) protrudes distally from the preservative unit.

15. A flow communication unit as in embodiment 14, wherein the preservative unit comprises a reservoir (255) with an amount of fluid preservative, the reservoir comprising a needle-penetrable septum portion (252) adapted to be penetrated by the hollow conduit distal portion (247) when the preservative unit (250) is moved from the first to the second position.

16. A flow communication unit as in embodiment 12, wherein the second flow way is in the form of a conduit (346) comprising an amount of fluid preservative, the conduit being sealed by a needle-penetrable septum.

17. A flow communication unit as in embodiment 16, further comprising:
a reservoir (350) with an amount of fluid preservative,
a preservative flow communication between the conduit (346) and the reservoir,
wherein the preservative flow communication is operatable between an initial open state and an operational closed state.

18. A flow communication unit as in embodiment 17, wherein the septum (352) is flexible and can be moved axially from an initial distal position to a proximal operational position to thereby close the preservative flow communication.

19. A flow communication unit (230, 330, 430) as in embodiment 12, wherein the flow conducting device flow inlet is an infusion set inlet.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An assembly comprising (a) a cartridge with a drug-filled interior, (b) a flow conducting device, and (c) a flow communication unit adapted to provide flow communication between the cartridge and the flow conducting device,
(a) the drug-filled cartridge comprising:
an outlet sealed by a needle-penetrable septum,
(b) the flow conducting device comprising:
a hollow tubular structure with a skin-piercing distal end, and
a proximal flow inlet,
(c) the flow communication unit comprising:
a proximal hollow needle adapted to penetrate the needle-penetrable septum,
a first flow way in flow communication with the proximal needle and comprising pressure-controlled valve structure,
a second flow way in flow communication with the first flow way,
an amount of preservative arranged to react with a substance received by the second flow way, and
distal flow communication structure adapted to provide flow communication between the second flow way and a flow conducting device flow inlet,
a tubular conduit comprising a distal portion with an open end, the tubular conduit forming the second flow way, and
a preservative unit comprising the amount of preservative and having a first axial position in which the tubular conduit distal portion is embedded in preservative, and a second axial position in which the tubular conduit distal portion protrudes distally from the preservative unit,
wherein the preservative unit is moved from the first position to the second position when the flow conducting device is connected to the flow communication unit, the tubular conduit distal portion thereby providing the distal flow communication structure,
whereby:
a combined flow way can be established between the cartridge interior and the hollow tubular structure via at least two of the proximal needle, the first flow way, and second flow way, when the cartridge, the flow communication unit and the flow conducting device are connected to each other,
the valve structure is controlled to open when the cartridge interior is pressurized, and
the preservative can react with a substance introduced to the second flow way via the hollow tubular structure with the skin-piercing distal end.

2. The assembly as in claim 1, wherein the flow conducting device is a needle unit, wherein the hollow tubular structure is a hollow expelling needle with the skin-piercing distal end.

3. The assembly as in claim 2, wherein the preservative unit comprises biasing structure moving the preservative unit from the second position to the first position when the needle unit is disconnected from the flow communication unit.

4. The assembly as in claim 2, wherein:
the needle unit comprises the hollow tubular structure comprising a proximal portion with an open end forming the proximal flow inlet, and
the second flow way is adapted to receive the tubular conduit proximal portion when the needle unit is connected to the flow communication unit.

5. The assembly as in claim 1, wherein the preservative unit comprises a reservoir with the amount of preservative.

6. The assembly as in claim 5, wherein the reservoir comprises a needle-penetrable septum portion adapted to be penetrated by the hollow conduit distal portion when the preservative unit is moved from the first position to the second position.

7. An assembly comprising (a) a cartridge with a drug-filled interior, (b) a flow conducting device, and (c) a flow communication unit adapted to provide flow communication between the cartridge and the flow conducting device,
(a) the drug-filled cartridge comprising:
an outlet sealed by a needle-penetrable septum,
(b) the flow conducting device comprising:
a hollow tubular structure with a skin-piercing distal end, and
a proximal flow inlet,
(c) the flow communication unit comprising:
a proximal hollow needle adapted to penetrate the needle-penetrable septum,
a first flow way in flow communication with the proximal needle and comprising pressure-controlled valve structure,
a second flow way in flow communication with the first flow way,
an amount of preservative arranged to react with a substance received by the second flow way, and
distal flow communication structure adapted to provide flow communication between the second flow way and a flow conducting device flow inlet,
whereby:
a combined flow way can be established between the cartridge interior and the hollow tubular structure via at least two of the proximal needle, the first flow way, and second flow way, when the cartridge, the flow communication unit and the flow conducting device are connected to each other,
the valve structure is controlled to open when the cartridge interior is pressurized, and
the preservative can react with a substance introduced to the second flow way via the hollow tubular structure with a skin-piercing distal end; wherein the flow conducting device is a needle unit, wherein the hollow tubular structure is a hollow expelling needle with the skin-piercing distal end; wherein: the needle unit comprises the hollow tubular structure comprising a proximal portion with an open end forming the proximal flow inlet, and
the second flow way is adapted to receive the tubular conduit proximal portion when the needle unit is connected to the flow communication unit;

wherein: the second flow way is in the form of a conduit comprising an amount of preservative, the conduit being closed by a septum adapted to be penetrated by the tubular conduit proximal portion when the needle unit is connected to the flow communication unit.

8. The assembly as in claim 7, wherein the flow communication unit comprises:
a reservoir with the amount of preservative,
a preservative flow communication between the conduit and the reservoir,
wherein the preservative flow communication is operated between an initial open state and an operational closed state when the needle unit is connected to the flow communication unit.

9. The assembly as in claim 8, wherein:
the flow communication unit comprises a septum structured to flex and move axially from an initial distal position to a proximal operational position to thereby close the preservative flow communication when the needle unit is connected to the flow communication unit.

10. A flow communication unit comprising:
a proximal hollow needle adapted to penetrate a needle-penetrable septum,
a first flow way in flow communication with the proximal needle and comprising pressure-controlled valve structure,
a second flow way in flow communication with the first flow way,
an amount of preservative arranged to react with a substance received by the second flow way, and
distal flow communication structure adapted to provide flow communication between the second flow way and a flow conducting device flow inlet,
a tubular conduit comprising a distal portion with an open end, the tubular conduit forming the second flow way, and
a preservative unit comprising the amount of preservative and having a first axial position in which the tubular conduit distal portion is embedded in preservative, and a second axial position in which the tubular conduit distal portion protrudes distally from the preservative unit,
wherein the preservative unit is moved from the first position to the second position when the needle unit is connected to the flow communication unit, the tubular conduit distal portion thereby providing the distal flow communication structure,
wherein the valve structure is controlled to open when the proximal hollow needle is pressurized.

11. The flow communication unit as in claim 10, wherein the flow conducting device flow inlet is a needle unit flow inlet.

12. The flow communication unit as in claim 11, wherein the preservative unit comprises a reservoir with the amount of preservative, the reservoir comprising a needle-penetrable septum portion adapted to be penetrated by the hollow conduit distal portion when the preservative unit is moved from the first to the second position.

13. The flow communication unit as in claim 12, wherein the second flow way is in the form of a conduit comprising an amount of fluid preservative, the conduit being sealed by a needle-penetrable septum.

\* \* \* \* \*